(12) United States Patent
Bergelin et al.

(10) Patent No.: US 9,120,220 B2
(45) Date of Patent: Sep. 1, 2015

(54) CONTROL OF A GLOVE-BASED GRASP ASSIST DEVICE

(75) Inventors: Bryan J Bergelin, Houston, TX (US); Chris A. Ihrke, Hartland, MI (US); Donald R. Davis, Novi, MI (US); Douglas Martin Linn, White Lake, MI (US); Adam M Sanders, Huntersville, NC (US); R. Scott Askew, Houston, TX (US); Evan Laske, Troy, MI (US); Kody Ensley, Polson, MT (US)

(73) Assignees: GM Global Technology Operations LLC, Detroit, MI (US); The United States of America As Represented by the Administrator of the National Aeronautics and Space Administration, Washington, DC (US)

( * ) Notice: Subject to any disclaimer, the term of this patent is extended or adjusted under 35 U.S.C. 154(b) by 856 days.

(21) Appl. No.: 13/408,675

(22) Filed: Feb. 29, 2012

(65) Prior Publication Data

US 2013/0226350 A1    Aug. 29, 2013

(51) Int. Cl.
| | |
|---|---|
| *G05B 13/00* | (2006.01) |
| *A41D 19/00* | (2006.01) |
| *B25J 9/00* | (2006.01) |
| *B25J 9/10* | (2006.01) |
| *B25J 13/08* | (2006.01) |
| *A61H 1/02* | (2006.01) |
| *A61B 5/11* | (2006.01) |
| *A61B 5/22* | (2006.01) |

(52) U.S. Cl.
CPC ............. *B25J 9/0006* (2013.01); *A61B 5/1107* (2013.01); *A61B 5/225* (2013.01); *A61H 1/0288* (2013.01); *B25J 9/104* (2013.01); *B25J 13/08* (2013.01); *A41D 19/0024* (2013.01); *A61H 2201/0184* (2013.01); *A61H 2201/1246* (2013.01); *A61H 2201/165* (2013.01); *A61H 2201/1638* (2013.01); *A61H 2201/5002* (2013.01); *A61H 2201/5061* (2013.01); *A61H 2201/5097* (2013.01); *A61H 2230/605* (2013.01)

(58) Field of Classification Search
None
See application file for complete search history.

(56) References Cited

U.S. PATENT DOCUMENTS

| | | | |
|---|---|---|---|
| 5,117,700 | A | 6/1992 | Trechsel |
| 5,845,540 | A | 12/1998 | Rosheim |
| 5,912,658 | A * | 6/1999 | Bergamasco et al. ......... 345/156 |
| 5,967,580 | A | 10/1999 | Rosheim |
| 6,042,555 | A * | 3/2000 | Kramer et al. ................ 600/595 |
| 6,658,962 | B1 | 12/2003 | Rosheim |
| 7,784,363 | B2 | 8/2010 | Ihrke et al. |
| 8,029,414 | B2 | 10/2011 | Ingvast et al. |
| 8,056,423 | B2 | 11/2011 | Abdallah et al. |
| 2010/0041521 | A1 * | 2/2010 | Ingvast et al. .................. 482/49 |

(Continued)

*Primary Examiner* — Ryan Jarrett
(74) *Attorney, Agent, or Firm* — Quinn Law Group, PLLC

(57) ABSTRACT

A grasp assist system includes a glove and sleeve. The glove includes a digit, i.e., a finger or thumb, and a force sensor. The sensor measures a grasping force applied to an object by an operator wearing the glove. The glove contains a tendon connected at a first end to the digit. The sleeve has an actuator assembly connected to a second end of the tendon and a controller in communication with the sensor. The controller includes a configuration module having selectable operating modes and a processor that calculates a tensile force to apply to the tendon for each of the selectable operating modes to assist the grasping force in a manner that differs for each of the operating modes. A method includes measuring the grasping force, selecting the mode, calculating the tensile force, and applying the tensile force to the tendon using the actuator assembly.

20 Claims, 2 Drawing Sheets

(56) References Cited

U.S. PATENT DOCUMENTS

| | | | |
|---|---|---|---|
| 2010/0121232 A1* | 5/2010 | Sankai | 601/23 |
| 2010/0152898 A1 | 6/2010 | Reiland et al. | |
| 2010/0280659 A1 | 11/2010 | Abdallah et al. | |
| 2010/0280662 A1 | 11/2010 | Abdallah et al. | |
| 2011/0071664 A1 | 3/2011 | Linn et al. | |
| 2011/0071678 A1 | 3/2011 | Ihrke et al. | |
| 2011/0208355 A1* | 8/2011 | Tsusaka | 700/246 |
| 2012/0317696 A1* | 12/2012 | Chapuis et al. | 2/160 |
| 2013/0072836 A1* | 3/2013 | Heaton et al. | 601/152 |
| 2013/0197399 A1* | 8/2013 | Montgomery | 600/595 |

* cited by examiner

CONTROL OF A GLOVE-BASED GRASP ASSIST DEVICE

STATEMENT REGARDING FEDERALLY SPONSORED RESEARCH OR DEVELOPMENT

This invention was made with government support under NASA Space Act Agreement number SAA-AT-07-003. The invention described herein may be manufactured and used by or for the U.S. Government for U.S. Government (i.e., non-commercial) purposes without the payment of royalties thereon or therefor.

TECHNICAL FIELD

The present disclosure relates to the control of a grasp assist device that may be worn as a glove by a human operator.

BACKGROUND

Repetitive motion can adversely affect product quality and process efficiency. Ergonomics is an evolving scientific discipline that ultimately seeks to understand and improve human interactions with the various pieces of equipment used within a work environment, e.g., keyboards, workstations, torque wrenches, control input devices, and the like. Good ergonomic design practices seek to optimize aspects of the physical work environment as they relate to the human operators working therein.

Certain work tasks may stress an operator in a manner that cannot be lessened by even the most optimal of ergonomic workplace configurations. For example, manual operations requiring a repetitive or sustained grasping of an object can stress an operator's hands, fingers, and forearms. As a result, an operator's grip strength and productivity can gradually decline over the course of a work day. Grip strength can also vary widely between different operators due to differences in physical stature, injury, and/or muscle fatigue. The variable nature of a given operator's grip strength may result in relatively inefficient execution of certain grasp-related work tasks.

SUMMARY

A system and a method are disclosed herein for controlling a glove-based grasp assist device. An operator may wear such a device on a hand and forearm. The grasp assist device in one embodiment may include multiple flexible tendons that are selectively tensioned with a calculated tensile force by a corresponding actuator assembly, for example a motorized ball screw assembly or a linear actuator. The actuator assembly pulls as needed on the tendon(s) to help close the digits of the operator's hand into a particular grasp pose. One or more force sensors are positioned with respect to the glove. The force sensor(s) provide force feedback signals to a controller. The controller calculates and commands the required tensile force from the various tendons.

In particular, a grasp assist system according to one embodiment includes a glove and a sleeve. The glove, which is wearable on a hand of an operator, includes a digit, i.e., a finger or thumb, a force sensor, and a flexible tendon. The force sensor is positioned with respect to the glove and measures a grasping force applied to an object by an operator wearing the glove. The tendon has a first end that is connected to the digit. The sleeve, which is wearable on a forearm of the operator, includes a controller and an actuator assembly that is connected to a second end of the tendon.

The controller includes a user interface, a configuration module having a recorded plurality of selectable operating modes, and a processor. The operating modes include at least one force-based control mode and at least one position-based control mode. The processor calculates a tensile force for each of the selectable operating modes. The controller is in communication with the force sensor on the glove and the actuator assembly in the sleeve. The controller is configured to receive a selected one of the operating modes via the user interface and to apply the calculated tensile force to the tendon via the actuator assembly.

A method for controlling a grasp assist system having a glove and a sleeve includes measuring, via a force sensor positioned with respect to the glove, a grasping force applied to an object by an operator wearing the glove. The method also includes selecting from a set of user-selectable operating modes using a user interface, including selecting from at least one force-based control mode and at least one position-based control mode, and calculating, via a controller, a tensile force to apply to a tendon for the selected operating mode. The tendon is routed through a finger or thumb of the glove. The method additionally includes applying the tensile force to the tendon using an actuator assembly to thereby assist an operator wearing the glove and sleeve in grasping the object.

The above features and advantages and other features and advantages of the present invention are readily apparent from the following detailed description of the best modes for carrying out the invention when taken in connection with the accompanying drawings.

DETAILED DESCRIPTION

Figure 1:
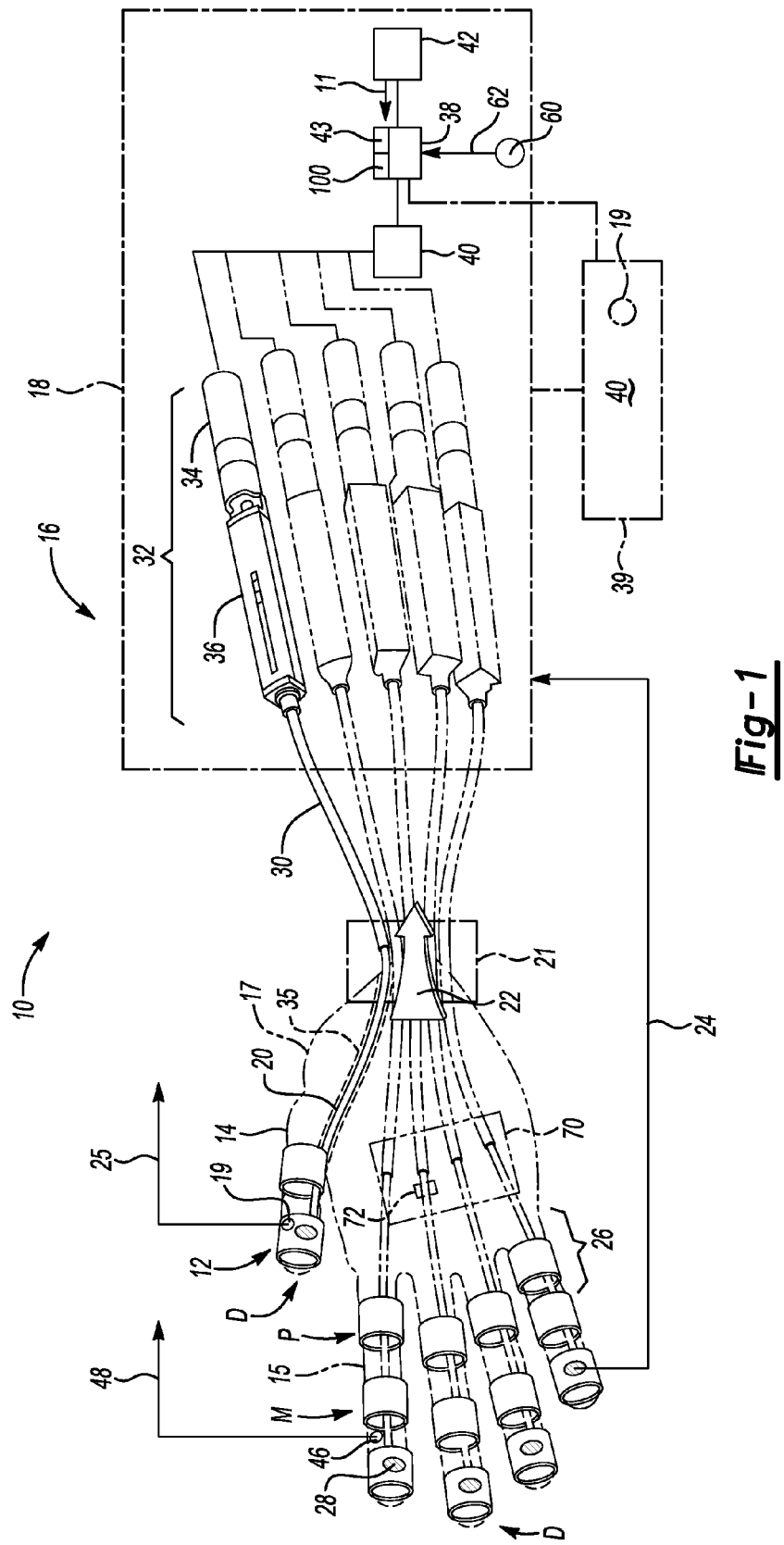
FIG. 1 is a schematic illustration of an example glove-based grasp assist device and associated controller configured to control the grasp assist device as set forth herein.
Figure 3:
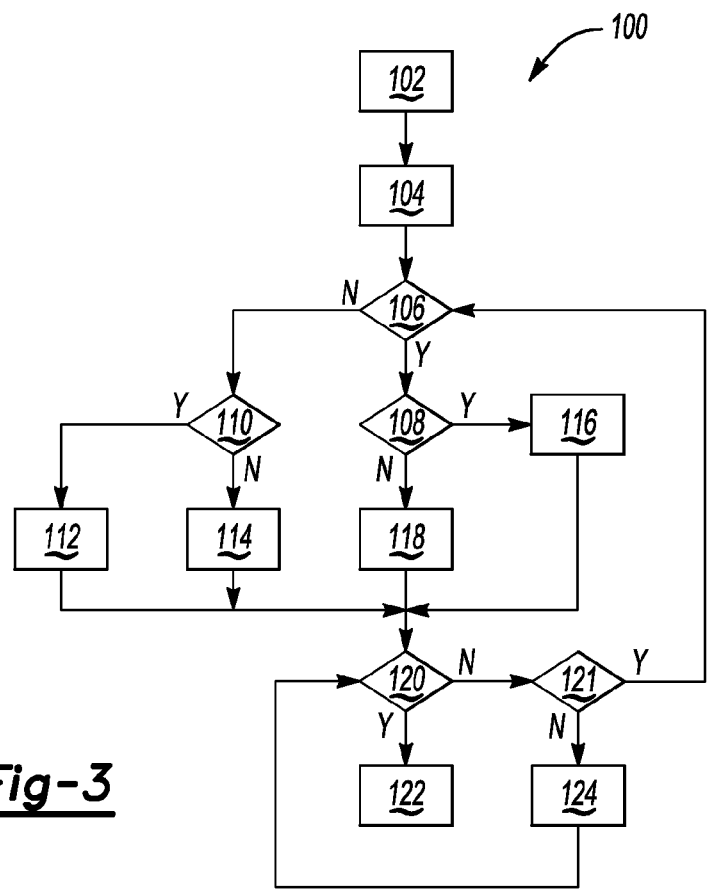
FIG. 3 is a flow chart describing an example method for controlling the grasp assist device shown in FIG. 1.

With reference to the drawings, wherein like reference numbers refer to the same or similar components throughout the several views, an example grasp assist system 10 is shown in FIG. 1. The system 10 includes a glove 12 and a sleeve 18. When worn by an operator on a hand and forearm, respectively, the glove 12 and sleeve 18 assist the operator in grasping an object. A controller 38 is used as part of the system 10 to calculate and apply a tensile force (arrow 22) to one or more flexible tendons 20. The controller 38 executes process instructions embodying the present control method 100, an example of which is shown in FIG. 3 and described in greater detail below.

The grasp assist device 10 of FIG. 1 may include a tendon drive system (TDS) 16 in one possible embodiment. The TDS 16 may be fully encased or contained at least partially within the sleeve 18. The TDS 16 may be linked to the glove 12 via the tendon(s) 20, with the augmenting tensile force (arrow 22) applied to some or all of the flexible tendons 20 in response to force feedback signals 24 received by the controller 38 from one or more force sensors 28 positioned with respect to the glove 12.

The glove 12 may include one or more digits, i.e., a thumb 14 and/or one or more fingers 15. The glove 12 may be configured as a conventional full four-finger/one thumb glove as shown, or with fewer fingers 15/no thumb 14 in other embodiments. Connected to the material 17 of the glove 12, for example sewn in place, may be a plurality of phalange rings 26 or another suitable load bearing structure. Each of the phalange rings 26 may at least partially circumscribe a digit of the operator's hand, i.e., by at least partially circumscribing a respective one of the thumb 14 or fingers 15 of the glove 12. Alternatively, the phalange rings 26 may be positioned within the thumb 12/fingers 15 of the glove 12. Thus, any tensile force (arrow 22) imparted by some or all of the tendons 20 can indirectly act on an operator's fingers/thumb through the phalange rings 26.

The force sensors 28 shown in FIG. 1 may be positioned with respect to the glove 12 such as at a medial portion or distal end of the thumb 14 and/or the finger(s) 15, or alternatively on a palm of the glove 12. Only one force sensor 28 may be used in an alternative embodiment. An optional on/off pressure switch 19 may be disposed on one or more of the thumb 14 and/or the fingers 15 to signal a desired grasp/grasp release, and to trigger a corresponding controlled application or discontinuation of the tensile force (arrow 22). The pressure switch 19 may be located in the alternative remotely from the device 10, e.g., on a larger belt-worn power pack 39 as shown in phantom. The force sensors 28 and the switch 19 may be connected to or formed integrally with a respective one of the phalange rings 26, such as the phalange rings positioned at the distal end of each finger 15 and thumb 14.

In general, a grasping force exerted on an object in the operator's grasp activates the force sensor(s) 28. The phalange rings 26 in turn are connected to the tendons 20 that run through the phalange rings 26, with at least some of the phalange rings 26 acting as guides for the tendons 20. Two types of phalange rings 26 may be provided herein: the phalange rings (arrow D) positioned at the distal end of each finger 15 and thumb 14, and respective medial (arrow M) and proximal (arrow P) phalange rings 26. The tendons 20 terminate at the distal (arrow D) phalange rings 26, while the medial (arrow M) and proximal (arrow P) phalange rings 26 are primarily used to guide or direct the tendons 20 and to support the operator's finger.

The force sensors 28 may be positioned and configured to sense only the grasping force applied by the operator to an object. In this embodiment, the force sensor(s) 28 may be positioned on an inner surface of the distal phalange rings 26 (arrow D). Other designs may also be used without departing from the intended scope of the control method 100 shown in FIG. 2 and described below.

When an object is grasped by an operator, the grasping force or pressure is measured by the force sensor(s) 28 and relayed as the set of force feedback signals 24 to the controller 38, which may be worn on/in the sleeve 18 of the grasp assist device 10 in one embodiment. Each of the force sensors 28 may be configured as a pressure transducer or any other suitable load or contact cell that precisely measures the amount of force between the force sensor 28 and any object grasped by the operator. An optional biometric sensor 60 as described below may be used to measure biometric information (arrow 62) with respect to an operator wearing the glove 12 and to transmit the measured information to the controller 38.

The TDS 16 shown in FIG. 1 is directly connected to each of the phalange rings 26 via the tendons 20, which are disposed and freely moveable within a flexible outer sleeve or conduit 30. In one embodiment, each of the tendons 20 may be configured as a braided polymer, which in turn may include a suitable fluorocarbon, in order to increase the wear life of each tendon. However, other materials may also be used without departing from the intended scope of the invention.

The tendons 20 of FIG. 1 may pass through a tendon concentrator 21, which may be located on or near the base of the palm or wrist area of the operator. The tendons 20 run through the conduit 30 for at least part of the lengths of the tendons 20, and freely between the tendon concentrator 21 and the phalange rings 26. This arrangement may help isolate the grasping assist motion to the area on the operator's hand from the fingertips to the base of the operator's palm, i.e., isolate the effect of any augmenting tensile force to the area between the tendon concentrator 21 and the phalange rings 26. From the finger side of the tendon concentrator 21 to the distal phalange rings 26, the tendons 20 may be contained in channels 35 embedded or contained within the material of the glove.

As shown in phantom, multiple actuator assemblies 32, for instance motorized ball screw devices to which the tendons 20 are attached, may be configured in an array within the TDS 16. Each assembly 32 acts on a corresponding tendon 20. When only one TDS 16 is used, the tendon concentrator 21 may be used to connect the tendons 20 leading from a thumb 14 and each finger 15 to a single actuator tendon, i.e., the tendon shown via solid lines in FIG. 1. In this case, the tendon concentrator 21 provides an area for the multiple tendons 20 to be connected to a single tendon.

Still referring to FIG. 1, the actuator assembly 32 may include a servo motor 34 and a drive assembly 36, e.g., a ball and screw-type device according to one embodiment. Operation of the TDS 16 is provided via the controller 38, which draws any required power from an energy supply 40. The energy supply 40 may be configured as a miniature battery pack, e.g., a lithium ion cell or cells, or any other relatively lightweight or low-mass energy storage device.

A user interface 42 may be connected to the sleeve 18 and placed in communication with the controller 38 to facilitate selection of the desired operating mode. The user interface 42 may be an operator-accessible control panel, touchpad, or touch screen allowing an operator to select a particular mode of operation from a displayed menu of available modes as set forth below with reference to FIG. 3. A grasp mode signal (arrow 11) from the user interface 42 may be transmitted to the controller 38 to indicate the requested grasp mode.

The controller 38 of FIG. 1 processes the set of feedback signals (arrow 24) in executing the present method 100. Computer-executable code embodying the method 100 may be recorded on tangible, non-transitory memory 43 of the controller 38, and executed thereby to calculate and select an optimal augmenting tensile force (arrow 22) in response to the values relayed via the feedback signals (arrow 24) and the user-selected operating mode, as well as to provide other control actions as set forth below with reference to FIG. 3. This augmenting tensile force (arrow 22) is then applied to some or all of the tendons 20 using the drive assembly 36 to assist the grasp of an operator wearing the device 10.

The controller 38 may include one or more integrated circuits, which may be augmented by various electronic devices such as voltage regulators, capacitors, drivers, timing crystals, communication ports, etc. The controller 38 may be a microcontroller using limited power and limited read only memory (ROM), random access memory (RAM), and/or electrically-programmable read only memory (EPROM), and any required input/output (I/O) circuit devices, as well as signal conditioning and buffer electronics.

A processor 52 is used to provide the required processing power. Individual control algorithms resident in the controller 38 or readily accessible thereby, including any algorithm(s) or code required for executing the present method 100, may be stored in memory, e.g., ROM, and automatically executed to provide the requested control functionality. The controller 38 also takes input from the user interface 42 as noted above via the grasp mode signal (arrow 11) to either initially set or change a previously requested grasp mode.

In a particular embodiment, the glove 12 of FIG. 1 may be used for rehabilitation, such as when an operator has suffered an injury which has weakened the operator's grasp strength. Augmentation of the grasp strength may be provided as set forth above. However, it may be desirable to monitor the operator's grasp strength and track changes in the grasp strength as the operator undergoes therapy.

To do this, a tendon tension sensor 72 of the type known in the art may be positioned with respect to a conduit 30 at the interface between the conduit 30 and the conduit anchor 70. Such a tension sensor 72 may include, for example, one or more strain gauges which measure a conduit compressive force acting on the tension sensor 72 whenever the tendon 20 is under tension. The tension sensor 72 can then communicate the measured strain to the controller 38, e.g., wirelessly via the transceiver module 59 described below.

Measurements taken by the tension sensor 72 may be translated into actual tensile force measurements by the controller 38. In turn, these tensile force measurements may be recorded and tracked by the controller 38 to evaluate progress of an operator's changing grasp strength, with or without augmentation via the actuator assemblies 32. While only one tension sensor 72 is shown in FIG. 1 for simplicity, a different sensor 72 could be used with each conduit 30 to precisely track progress of an operator's grasp strength h respect to each of the operator's fingers and thumb during rehabilitation.

Figure 2:
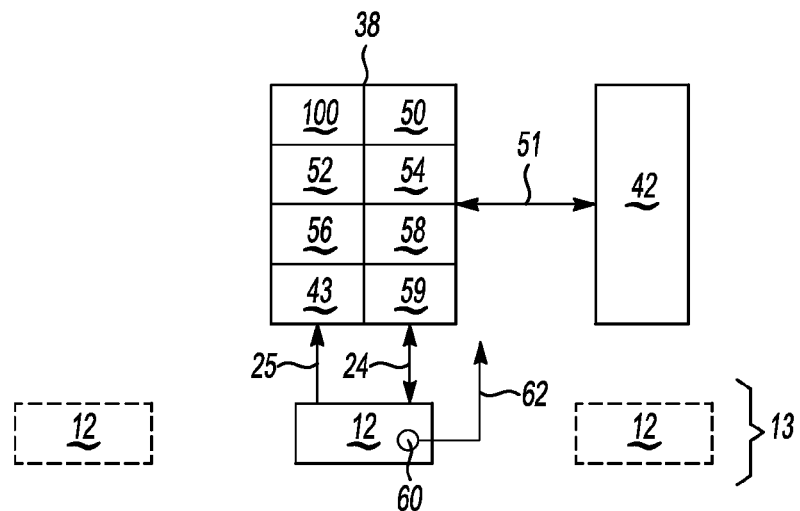
FIG. 2 is a schematic illustration of an example controller for use with the example grasp assist device shown in FIG. 1.

Referring to FIG. 2, the controller 38 of FIG. 1 is shown schematically to illustrate some of the control modules that may be used in various embodiments. The controller 38 is represented as a single unit in FIG. 2 for illustrative clarity. However, those of ordinary skill in the art will appreciate that some control modules of the controller 38 may be located remotely with respect to the glove 12. For example, a central server located in a plant may communicate with a network 13 of several gloves 12 as shown in phantom. Such an embodiment when used in conjunction with the biometric sensor 60 may enable the remote monitoring of the health and/or performance of individual operators and/or individual gloves 12, which may facilitate scheduling or rotation of personnel or maintenance of the gloves 12.

As noted above, the controller 38 of FIG. 2 includes memory 43, a processor 52, and computer-executable instructions embodying the present method 100. Additionally, the controller 38 may include a user configuration module 50, a biometric monitoring unit 54 that receives the biometric information (arrow 62) from the biometric sensor 60, an override module 56, a database management system (DBMS) 58, and/or a transceiver module 59. Each of these will now be explained in turn with reference to the structure of FIG. 1.

After an operator initially puts on the glove 12 and sleeve 18 of FIG. 1, the operator can select a desired operating mode via the user interface 42. As explained below with reference to FIG. 3, the controller 38 may be configured to execute one of a plurality of different operating modes, with each operating mode tied to a specific force-based or position-based control scheme. The user interface 42 may display a menu of options from which the operator can select. For instance, the operator can select a mode via a touchpad or other suitable input device, which the configuration module 50 records and executes in conjunction with the processor 52. The configuration module 50 may be embodied as control logic and associated hardware suitable for executing the various separate control options, possibly including a separate rehabilitation module using the tension sensor(s) 72 as described above.

Various options exist for optimizing the control of the grasp assist system 10 of FIG. 1 using the optional biometric information (arrow 62). For instance, the biometric sensor 60 may be configured as an electromyography (EMG) sensor that is used to customize the performance of the controller 38 in executing a particular operating mode. In such an embodiment, detected activity in the grasping muscles of the operator can be used to signal closing of the glove 12, and detected activity in the user's release muscles can be used to open the glove 12. Similar information can be used to detect muscle fatigue. The processor 52 can analyzes the EMG signals from the biometric sensor 60, and a warning could be generated indicating the operator should be rotated to a different task.

The override module 56 shown in FIG. 2 may provide a means of cancelling out of or overriding any grasp assist operation. For instance, the override module 56 may include a power switch which an operator can trip to cut power to the grasp assist device 10, e.g., the on/off switch 19 of FIG. 1, thus allowing the operator's hand to be manually opened without motor resistance. The override module 56 may also include a feedback path to the force sensor(s) 28, such that discontinuation of applied pressure as sensed by the force sensor(s) 28 can trigger a smooth ramp down of the grasp assist tension applied by the TDS 16. In yet another embodiment, the override module 56 may be configured to automatically cut power to the device 10 in response to a received signal from a remote device, e.g., a centrally generated emergency signal, a signal from an emergency stop button or other device, etc.

The DBMS 58 may be used in some embodiments to track the work history of a particular operator with respect to the glove 12 worn by that operator, the operator's tasks when wearing the glove 12, and other factors. When used in a distributed environment, e.g., one with multiple gloves 12 in operation in various locations of a plant, the DBMS 58 may enable useful data logging and analysis. Using the DBMS 58, trends may be readily detected and quickly acted upon as needed. For example, if an operator wearing a glove 12 operates normally with a threshold low amount of grasp assist for a few hours of a given work shift, followed by a progressive increase in the amount of grasp assist being provided, a supervisor may be alerted to the declining performance, which may be indicative of fatigue, and take appropriate action. Biometric information (arrow 62) from the biometric sensor 60 may likewise be recorded and analyzed in real time to determine fatigue and operator performance.

The transceiver module 59 of FIG. 2 may wirelessly transmit to, as well as receive from, any other device having a similar module, e.g., a centralized production management system, the DBMS 58, or a system dedicated to monitoring and tracking quality, worker health and safety, and the like. The controller 38 is not limited to the described modules, and need not use every described module to function. Therefore, the controller 38 of FIG. 2 is one possible embodiment for controlling the grasp assist device 10 shown in FIG. 1.

Referring to FIG. 3, in an example embodiment the method 100 begins at step 102 after an operator inserts a hand into the glove 12 and securely fastens the sleeve 18. Step 102 may entail zeroing the controller 38 by deleting old buffer data from any previous work sessions. Once properly zeroed, the method 100 proceeds to step 104.

At step 104, the controller 38 of FIG. 2 receives an input signal from the operator identifying the desired operating mode, i.e., the grasp mode signal (arrow 11) of FIG. 1. The controller 38 may be programmed with a variety of different force-based and position-based control modes from which the operator may select, or that may be automatically selected for the operator depending on the nature of the work task to be assisted. The method 100 proceeds to step 106 once the particular mode has been received by the controller 38.

At step 106 the controller 38 determines whether the received mode is a force-based control mode. The method 100 proceeds to step 108 if the received mode is a force-based control mode. If the received mode is not a force-based mode, the controller 38 determines that a position-based mode has been selected, and proceeds in the alternative to step 110.

At step 108, having determined at step 106 that the operator desires a force-based control mode, the controller 38 of FIG. 2 determines whether the operator has selected a constant force assist mode. If so, the method 100 proceeds to step 116. Otherwise, the method 100 proceeds to step 118.

At step 110, having determined at step 106 that the operator desires a position-based control mode, the controller 38 of FIG. 2 next determines whether the operator has selected a pre-configured grasp position mode. If so, the method 100 proceeds to step 112. Otherwise, the method 100 proceeds to step 114.

At step 112, the controller 38 actuates the tendons 20 to thereby move the fingers 15 and/or thumb 14 into the specific grasp pose called out by the pre-configured grasp position mode. When the glove 12 of FIG. 1 is instructed to close, the actuator assembly 32 of FIG. 1 moves the fingers 15/thumb 14 to a position or a sequence of positions, e.g., based on encoder counts, corresponding to a closed position.

Step 112 may entail precisely posing the fingers 15 and/or the thumb 14 into a particular position or positions with less/no emphasis on the amount of force applied by the fingers 15 and/or thumb 14. For instance, some grasp poses may require little additional force, but the repetitive nature of the pose may still cause fatigue over time, thus making it difficult for the operator to hold that particular pose over any length of time. A pre-configured grasp position or sequence of positions may facilitate repetition of such a pose, or may be of particular benefit in rehabilitation.

In other approaches, an optional position sensor 46 as shown in phantom may be positioned with respect to one or more of the fingers 15, and configured to measure the rotational angle of the finger 15 to which the sensor 46 is connected. Such a sensor 46 could be attached to the glove 12 and positioned on an axis of a finger joint of the operator, such that rotation of that joint is measured by the sensor 46 and relayed to the controller 38. Such positional information (arrow 48) could be used in a feedback loop to control the closing position of the monitored finger 15.

That is, if the pre-configured position includes a calibrated joint angle, the controller 38 can monitor the changing angle using the positional information (arrow 48) to determine when to discontinue tensioning of the tendon 20 for that particular finger 15. In other embodiments open loop control may be used, e.g., via a selected command or current to the actuator assemblies 32. Other sensors such as tension sensors (not shown) may also be used to collect more accurate information on the present state of the tendons 20 and position of the fingers 15 and/or thumb 14. The method 100 then proceeds to step 120.

At step 114, the controller 38 of FIG. 2 executes pseudo-force control, a mode in which the fingers 15/thumb 14 are closed to a position that is based on force input from the force sensor(s) 28 of FIG. 1. In true force-based control, actuators are controlled to maintain a desired force. This would work in a configuration of the glove 12 of FIG. 1 in which there are force sensors 28 located in the fingers 15/thumb 14 that are being actuated. The controller 38 would use the force feedback from a given finger 15, for instance, to move the actuator assembly 32 for that finger 15 such that the desired force measured by the force sensor 28 for that finger 15 was maintained.

In some embodiments, the force sensors 28 may not be used in the fingers 15, but instead only on the thumb 14. The thumb 14 may or may not be activated by a tendon 20. For pseudo-force control in such an embodiment, the fingers 15 would close to a configured grasp position for a nominal force detected by the force sensor 28 positioned on the thumb 14. For lighter forces on the thumb sensor, the fingers 15 could be actuated slightly less, e.g., based on encoder counts, and for greater forces on the thumb sensor the fingers 15 could be actuated slightly more. In other words, any of the fingers 15 or thumb 14 of the glove 12 that do not include the single force sensor 28 are moved to a position based on the force measured by the force sensor 28. This approach is distinctly different than pure force-based control because there is no force feedback on the fingers 15 being actuated. The method 100 proceeds to step 120 after completing step 114.

At step 116, the controller 38 of FIG. 2 closes the fingers 15 and/or thumb 14 of the glove 12 with a constant force, and then proceeds to step 120. Step 116 may entail measuring the apply force via the force sensor(s) 28 for each finger 15/thumb 14 having such a force sensor 28, comparing the measured values to a calibrated force in a closed-loop to determine the difference, and then setting the tensile force (arrow 22 of FIG. 1) applied to the various tendons 20 as the calculated difference. The method 100 then proceeds to step 120.

At step 118 the controller 38 of FIG. 2 executes a finger sensor feedback mode. In this mode, the tendons 20 are tensioned in such a manner that the fingers 15 and/or thumb 14 close when any one of the force sensors 28 detects a force. Depending on the embodiment, the grasp may be released when the force is no longer detected, or the grasp may be held until the grasp is released by other means, e.g., the switch 19 of FIG. 1. The method 100 then proceeds to step 120.

At step 120, the controller 38 continues execution of the requested mode while checking for a predetermined interrupt signal from the override module 56. Interrupt signals can include a power cut, off switch position, e.g., of the on/off switch 19 of FIG. 1, override, biometric information (arrow 62) from the biometric sensor 60 of FIGS. 1 and 2, and/or release of a given force sensor 28, depending on configuration and selected operating mode. If an interrupt signal is received, the method 100 proceeds to step 122. The method 100 instead proceeds to step 121 if an interrupt signal is not received.

At step 121, the controller 38 of FIG. 2 determines whether an operator wishes to change from one grasp mode to another. For instance, in using the grasp assist device 10 of FIG. 1 an operator may be able to switch between any modes during execution of a given task, either through operator input via the user interface 42 or a predetermined set of different grasps. An operator's task can require many different types of grasps to be performed.

Thus, step 121 may include detecting a changed grasp mode by examining the grasp signal (arrow 11) and comparing it to the present mode. The controller 38 repeats step 106 if at step 121 a new grasp mode signal (arrow 11) is received. If a new grasp mode signal (arrow 11) is not received at step 121, the controller 38 proceeds instead to step 124.

At step 122, the controller 38 executes a first control action. Step 122 may entail interrupting the grasp assistance in response to the interrupt signal detected at step 120. Interruption may progress in a manner that is appropriate in light of the particular interrupt mode. For instance, an emergency interrupt may require an immediate discontinuation of all tensile force (arrow 22 of FIG. 1). Other modes may gradually ramp down the tensile force to provide a smooth, transitioned release of the grasp. The controller 38 then repeats step 120 in a loop to determine if the interrupt condition has ceased.

At step 124, the controller 38 of FIG. 2 executes a second control action in which the controller 38 continues to provide the requested grasp assistance. The controller 38 activates the drive assembly 36 of FIG. 1. In an embodiment utilizing a ball screw or other electromechanical device, step 122 may include transmitting a signal from the controller 38 to the energy supply 40 of FIG. 1, or to a relay or switch in a power circuit of the energy supply 40 to thereby energize the ball screw or other device. The controller 38 then repeats step 120 in a loop until some type of end signal is received signaling an end to desired grasp assistance.

While the best modes for carrying out the invention have been described in detail, those familiar with the art to which this invention relates will recognize various alternative designs and embodiments for practicing the invention within the scope of the appended claims.

The invention claimed is:

1. A grasp assist system comprising:
a glove that is wearable on a hand of an operator, including:
a digit, wherein the digit is one of a thumb and a finger;
a force sensor positioned with respect to the glove, wherein the force sensor is configured to measure a grasping force applied to an object by an operator wearing the glove;
a tendon having a first end and a second end, wherein the first end is connected to the digit; and
a sleeve that is wearable on a forearm of the operator and having:
actuator assembly connected to the second end of the tendon; and
a controller including:
a user interface;
a configuration module having a recorded plurality of selectable operating modes, including at least one force-based control mode and at least one position-based control mode; and
a processor configured to calculate a tensile force for each of the selectable operating modes;
wherein the controller is in communication with the sensor and the actuator assembly, and is configured to receive a selected one of the selectable operating modes via the user interface and apply the tensile force to the tendon via the actuator assembly for the selected operating mode.

2. The system of claim 1, wherein the force sensor is positioned with respect to the digit.

3. The system of claim 1, wherein the force sensor is positioned with respect to a palm of the glove.

4. The system of claim 1, further comprising a biometric sensor in communication with the controller that is configured to measure biometric information of the operator, wherein the controller includes a biometric monitoring unit in communication with the biometric sensor that controls an operation of the glove using the measured biometric information.

5. The system of claim 4, wherein the biometric sensor is an electromyography sensor.

6. The system of claim 1, further comprising: at least one on/off switch in communication with the controller that alternatively enables and disables application of the tensile force.

7. The system of claim 1, wherein the at least one force-based control mode includes a mode in which the tendon is tensioned by the actuator assembly with a constant force.

8. The system of claim 1, wherein the at least one position-based control mode includes a mode in which the glove is moved to a pre-configured grasp position.

9. The system of claim 1, further comprising a database management system that records performance data of the glove.

10. The system of claim 1, including a plurality of the digits, wherein:
the force sensor is a single force sensor connected to one of the plurality of digits; and
the at least one force-based control mode is a pseudo-force control mode in which any of the digits to which the single sensor is not connected are moved to a position based on the force measured by the single sensor.

11. The system of claim 1, further comprising a tension sensor positioned with respect to the glove and configured to measure an actual tensile force acting on the tendon.

12. The system of claim 1, further comprising a position sensor that is positioned with respect to the digit, and configured to measure a rotational angle of the digit, wherein the controller is configured to use the measured rotational angle to control the closing position of the digit.

13. A grasp assist system comprising:
a glove having:
five digits, including four fingers and a thumb;
a force sensor positioned with respect to the thumb that is configured to measure a grasping force applied to an object by an operator wearing the glove;
four flexible tendons, wherein a corresponding first end of each of the four tendons is connected to a corresponding one of the four fingers; and
a sleeve containing a controller that is in communication with the sensor, a user interface that displays a recorded plurality of selectable operating modes to the operator and that receives a selected one of the selectable operating modes via the user interface, and four actuator assemblies each connected to a corresponding second end of a different one of the four tendons, wherein the controller is in communication with the force sensor and the actuator assemblies, and includes:
a configuration module having the recorded plurality of selectable operating modes, including at least one force-based control mode and at least one position-based control mode; and
a processor configured to calculate a tensile force to apply to at least one of the four tendons for each of the selectable operating modes;
wherein the controller is configured to receive the selected operating mode from the user interface and to apply the tensile force for the selected operating mode to the at least one of the four tendons via a corresponding one of the actuator assemblies.

14. The system of claim 13, wherein the glove includes a biometric sensor in communication with the controller, and wherein the controller includes a biometric monitoring unit that controls an operation of the glove at least in part as a function of biometric information measured by the biometric sensor.

15. The system of claim 13, wherein the glove includes a tension sensor configured to measure an actual tensile force applied to the tendons.

16. The system of claim 13, wherein the at least one force-based control mode includes a mode in which the fingers are moved with a constant force.

17. The system of claim 13, further comprising a database management system that monitors and records performance data of a glove and correlates the recorded performance data with a particular operator wearing the glove.

18. A method for controlling a grasp assist system having a glove and a sleeve, the method comprising:
   measuring, via a force sensor positioned with respect to the glove, a grasping force applied to an object by an operator wearing the glove;
   selecting from a set of user-selectable operating modes using a user interface, including selecting from at least one force-based control mode and at least one position-based control mode;
   calculating, via a controller, a tensile force to apply to a tendon for the selected operating mode, wherein the tendon is routed through a finger of the glove; and
   applying the tensile force to the tendon using an actuator assembly to thereby assist an operator wearing the glove and sleeve in grasping the object.

19. The method of claim 18, wherein the grasp assist system includes a biometric sensor in communication with the controller, the method further comprising:
   measuring biometric information of the operator using the biometric sensor; and
   controlling an operation of the glove at least in part as a function of biometric information as measured by the biometric sensor.

20. The method of claim 18, wherein the grasp assist system includes a position sensor that is positioned with respect to a digit of the glove and configured to measure a rotational angle of the digit, and wherein the controller is configured to use the measured rotational angle to control a position of the digit.

* * * * *